(12) United States Patent
Shah et al.

(10) Patent No.: US 12,193,844 B1
(45) Date of Patent: Jan. 14, 2025

(54) MOLDING PROCESS FOR A CRANIAL IMPLANT AND THE CRANIAL IMPLANT RESULTING THEREFROM

(71) Applicant: LONGEVITI NEURO SOLUTIONS LLC, Baltimore, MD (US)

(72) Inventors: Jimmy Shah, Philadelphia, PA (US); Corbin Clawson, Hampstead, MD (US); Jeffrey Thomas Waclawski, Essex, MD (US); Jesse Christopher, Hunt Valley, MD (US)

(73) Assignee: LONGEVITI NEURO SOLUTIONS LLC, Baltimore, MD (US)

( * ) Notice: Subject to any disclaimer, the term of this patent is extended or adjusted under 35 U.S.C. 154(b) by 94 days.

(21) Appl. No.: 18/149,849

(22) Filed: Jan. 4, 2023

Related U.S. Application Data

(60) Provisional application No. 63/266,396, filed on Jan. 4, 2022.

(51) Int. Cl.
*B29C 39/00* (2006.01)
*A61B 5/00* (2006.01)
(Continued)

(52) U.S. Cl.
CPC ............ *A61B 5/6868* (2013.01); *A61B 5/293* (2021.01); *A61B 5/37* (2021.01); *B29C 33/3835* (2013.01);
(Continued)

(58) Field of Classification Search
CPC ............ B29C 33/3835; B29C 33/3842; B29C 33/3857; B29C 33/3892; B29C 39/00; B29C 39/02; B29C 39/021
See application file for complete search history.

(56) References Cited

U.S. PATENT DOCUMENTS 3,048,537 A 8/1962 Pall et al.
5,741,215 A 4/1998 D'Urso
(Continued)

FOREIGN PATENT DOCUMENTS

JP 5746206 B2 5/2015
WO 201746300 A1 3/2017

OTHER PUBLICATIONS

Aatman M. Shah, Henry Jung, & Stephen Skirboll, Materials Used in Cranioplasty: A History and Analysis, Neurosurg Focus, vol. 36, Apr. 2014, pp. 1-7.

*Primary Examiner* — Thu Khanh T. Nguyen
(74) *Attorney, Agent, or Firm* — Welsh Flaxman & Gitler LLC

(57) ABSTRACT

A two-part molding process includes creating a computer-based design, creating a master of the cavity implant and a master of the cap implant, creating a first mold, a second mold, and a third mold, casting the cavity implant from resin, curing the cavity implant, removing the cavity implant from the first mold and the second mold, drilling a hole through the second mold, placing the cavity implant on the second mold and placing components of a powered data management module within respective cavities, placing uncured resin on the cavity implant and components of the powered data management module, curing the resin, preparing the components of the powered data management module for casting, casting the cap implant, wherein the third mold is directly secured to the second mold and the second mold and the third mold are placed in a press, curing the cap implant, and removing the cranial implant.

20 Claims, 12 Drawing Sheets

(51) Int. Cl.
*A61B 5/293* (2021.01)
*A61B 5/37* (2021.01)
*B29C 33/38* (2006.01)
*B29C 39/02* (2006.01)

(52) U.S. Cl.
CPC .......... B29C 33/3842 (2013.01); B29C 39/02 (2013.01); *A61B 2562/046* (2013.01); *A61B 2562/125* (2013.01)

(56) References Cited

U.S. PATENT DOCUMENTS

| | | |
|---|---|---|
| 6,112,109 A | 8/2000 | D'Urso |
| 6,726,678 B1 | 4/2004 | Nelson et al. |
| 6,932,842 B1 | 8/2005 | Litschko et al. |
| 7,212,864 B2 | 5/2007 | Wahlstrand et al. |
| 7,242,982 B2 | 7/2007 | Singhal et al. |
| 7,392,089 B2 | 6/2008 | Wahlstrand et al. |
| 7,529,586 B2 | 5/2009 | Wahlstrand et al. |
| 7,596,399 B2 | 9/2009 | Singhal et al. |
| 7,596,408 B2 | 9/2009 | Singhal et al. |
| 7,747,305 B2 | 6/2010 | Dean et al. |
| 7,848,817 B2 | 12/2010 | Janzig et al. |
| 7,881,796 B2 | 2/2011 | Scott et al. |
| 8,086,336 B2 | 12/2011 | Christensen |
| 8,974,535 B2 | 3/2015 | Antonyshyn et al. |
| 9,162,072 B2 | 10/2015 | Singhal et al. |
| 9,764,510 B2 | 9/2017 | Antonyshyn et al. |
| 9,993,337 B1 | 6/2018 | Brogan et al. |
| 10,912,648 B2 * | 2/2021 | Gordon .................. B33Y 10/00 |
| 11,154,401 B2 | 10/2021 | Antonyshyn et al. |
| 2009/0281623 A1 | 11/2009 | Kast et al. |
| 2012/0010711 A1 | 1/2012 | Antonyshyn et al. |
| 2019/0038415 A1 | 2/2019 | Heunen et al. |

* cited by examiner

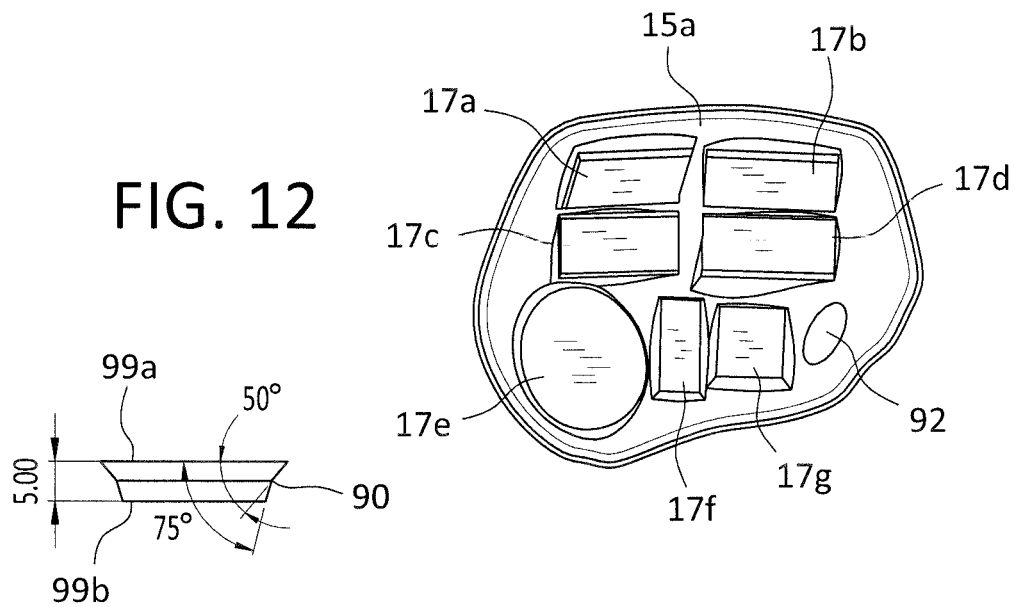
FIG. 12
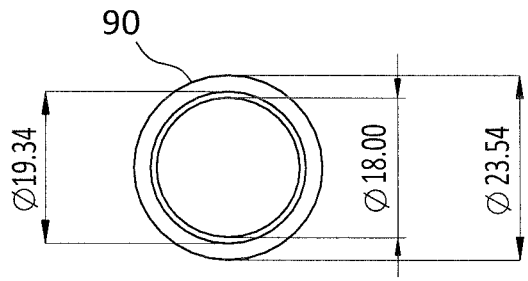
FIG. 13A
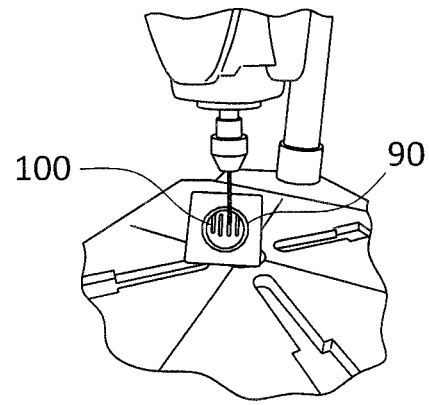
FIG. 13C
FIG. 13B
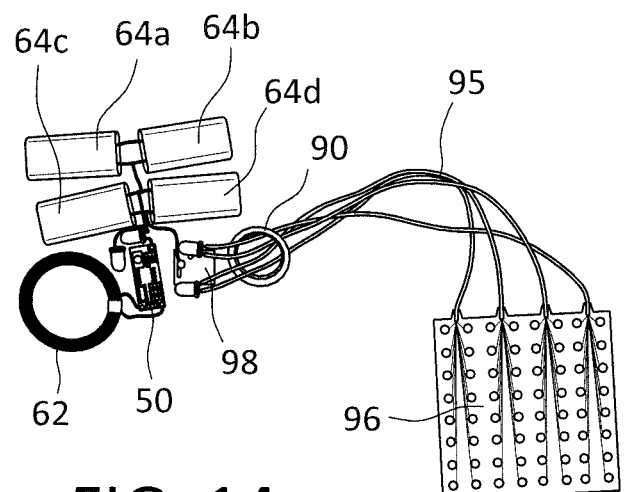
FIG. 14

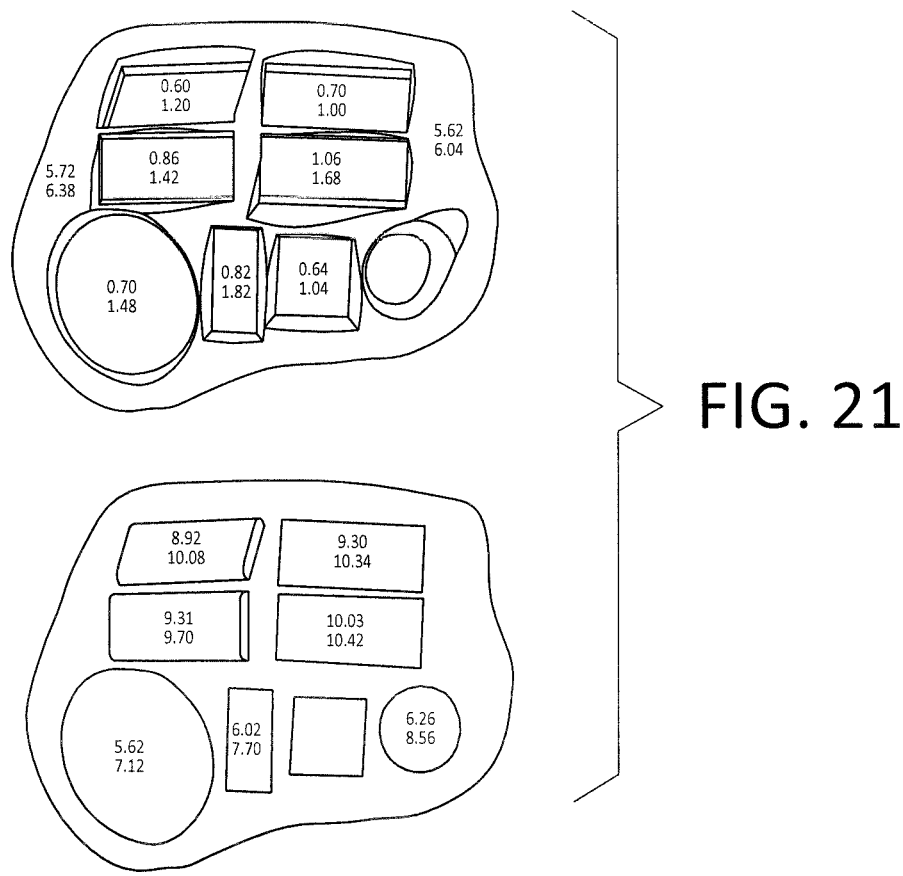
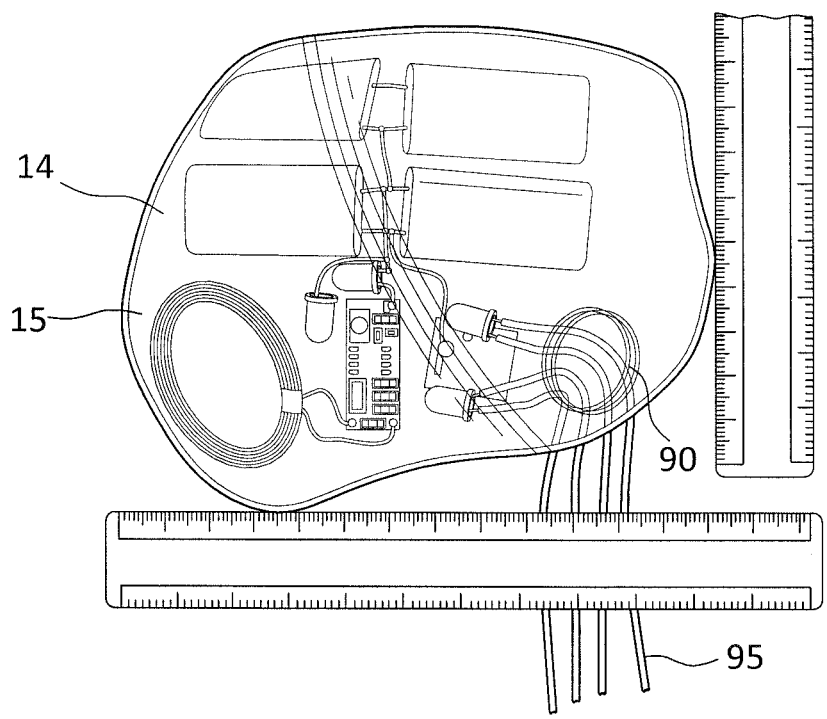
FIG. 21
FIG. 22

MOLDING PROCESS FOR A CRANIAL IMPLANT AND THE CRANIAL IMPLANT RESULTING THEREFROM

CROSS REFERENCE TO RELATED APPLICATION

This application claims the benefit of U.S. Provisional Patent Application Ser. No. 63/266,396, entitled "MOLDING PROCESS FOR A CRANIAL IMPLANT AND THE CRANIAL IMPLANT RESULTING THEREFROM," filed Jan. 4, 2022, which is incorporated herein by reference.

BACKGROUND OF THE INVENTION

1. Field of the Invention

The present invention relates to a molding process for a cranial implant and the cranial implant resulting therefrom.

2. Description of the Related Art

The development of cranial implants integrating functional neurosurgical implants as disclosed in Applicant's own U.S. Pat. No. 10,912,648, entitled "METHOD FOR MANUFACTURING A LOW-PROFILE INTERCRANIAL DEVICE AND THE LOW-PROFILE INTERCRANIAL DEVICE MANUFACTURED THEREBY," which is incorporated herein by reference, has led to new treatment possibilities by combining cranial reconstruction with neurosurgical approaches in a single-stage procedure.

The present invention advances these prior developments by providing a process for molding cranial implants in a manner allowing for the integration of functional neurosurgical implants.

SUMMARY OF THE INVENTION

It is an aspect to provide a two-part molding process. The molding process comprises creating a computer-based design of a cranial implant including a cavity implant and a cap implant, creating a first mold, a second mold, and a third mold, casting the cavity implant from resin, curing the cavity implant, and removing the cavity implant from the first mold and the second mold. The method also includes drilling a hole through the second mold where electrode leads are to exit the cavity implant, placing the cavity implant on the second mold and placing components of a functional neurological implant within respective cavities, placing uncured resin on the cavity implant and components of the functional neurological implant, lowering the third mold onto the second mold, closing the second and third molds and curing the resin. The method also includes preparing the components of the functional neurological implant for casting, casting the cap implant, wherein the third mold is directly secured to the second mold and the second mold and the third mold are placed in a press, and curing the cap implant. Finally, the cranial implant is removed and tested.

In some embodiments the resin is PMMA.

In some embodiments creating the first mold, the second mold, and the third mold includes forming the first mold around an outer surface of a master of the cavity implant, molding the second mold around sides and inner surface of the master of the cavity implant, and casting the third mold based upon the second mold.

In some embodiments casting the cavity implant from resin includes spreading the resin to mostly fill an impression of the first mold, placing and securing the second mold directly over the first mold, applying pressure to the first mold and the second mold, and removing the first mold and the second mold.

In some embodiments the method further includes creating a master of the cavity implant and a master of the cap implant.

In some embodiments the method further includes, after curing the cavity implant, sanding the cavity implant.

In some embodiments the method further includes, after placing the cavity implant on the second mold and placing components of the functional neurological implant within respective cavities, passing an electrode grid is through a bottom of the cavity implant, down the hole in the second mold, and out to an exterior of the second mold.

In some embodiments the electrode grid is secured to an outside of the second and third molds to prevent it from becoming tangled.

In some embodiments the method further includes, after preparing the components of the functional neurological implant for casting, feeding an electrode grid housing through the cavity implant and through the hole in the second mold and subsequently lowering the components of the powered data management module into cavities within the cavity implant.

In some embodiments the method further includes modifying the second mold to accommodate an electrode grid housing.

In some embodiments modifying includes placing a master of the cavity implant on the second mold, marking a location of an electrode plug hole on the second mold, and drilling a hole through the second mold.

In some embodiments the molding process is for manufacturing an implantable data management and energy system that includes a functional neurological implant, a powered data management module mounted within the cranial implant, and a data storage and processing unit.

In some embodiments the powered data management module includes a multi-channel input/output, a transmitter, and a power system comprised of a power receiver and batteries.

In some embodiments the functional neurological implant is a neurological device implanted to abut neurologic tissue.

In some embodiments the data storage and processing unit is a neurological data processing mechanism capable of receiving, storing, and/or processing neurological data sensed by the functional neurological implant.

In some embodiments the data storage and processing unit provides status information regarding the functional neurological implant, such as battery charge, data transmission rate, and alerts if there are any issues with data integrity.

In some embodiments the functional neurological implant and the powered data management module are connected using electrical cabling.

In some embodiments the data storage and processing unit is wirelessly linked to the data storage and processing unit.

In some embodiments the functional neurological implant includes brain mapping functionality.

In some embodiments the powered data management module comprises a data management system and a power system.

In some embodiments the functional neurological implant is a powered data management module.

Other objects and advantages of the present invention will become apparent from the following detailed description

BRIEF DESCRIPTION OF THE DRAWINGS

FIGS. 5 to 22 are various views used in disclosing the manufacturing process, wherein FIG. 5 is a top view showing the cavity implant without the electronic components therein. The cavity implant has an overall implant thickness is 5.5 mm. The bases of the cavities are at least 0.5 mm from the inner surface of the implant. The cavities were created using component cutters. The design of the component cutters allowed chamfers and tolerances to be integrated within the cavity implant.

FIG. 6 is a top view showing the cavity implant with the electronic components therein.

FIG. 7 is a top plan view of the cap implant.

FIG. 9 shows an X-ray and a side view of a skull showing the position of the cranial implant within the skull.

FIG. 12 is a top view of a cavity implant after a first curing cycle.

FIGS. 13A, 13B, and 13C respectively show a side view of the electrode plug, a bottom view of the electrode plug, and a perspective view of an electrode plug being drilled with holes.

FIG. 14 is a top view of an electronic assembly.

FIG. 15 is a top view of the second mold after the formation of a hole therein.

FIG. 16 shows views of the second and third molds.

FIG. 17 shows the cranial implant after the second curing cycle.

FIG. 18 shows the cranial implant from above and below after sanding and polishing.

FIG. 19 shows testing of the cranial implant.

FIG. 20 shows a lateral and front view of the cranial implant fitted within a skull model.

FIGS. 21 and 22 show measurement testing of the resulting cranial implant.

DESCRIPTION OF THE PREFERRED EMBODIMENTS

Figure 1:
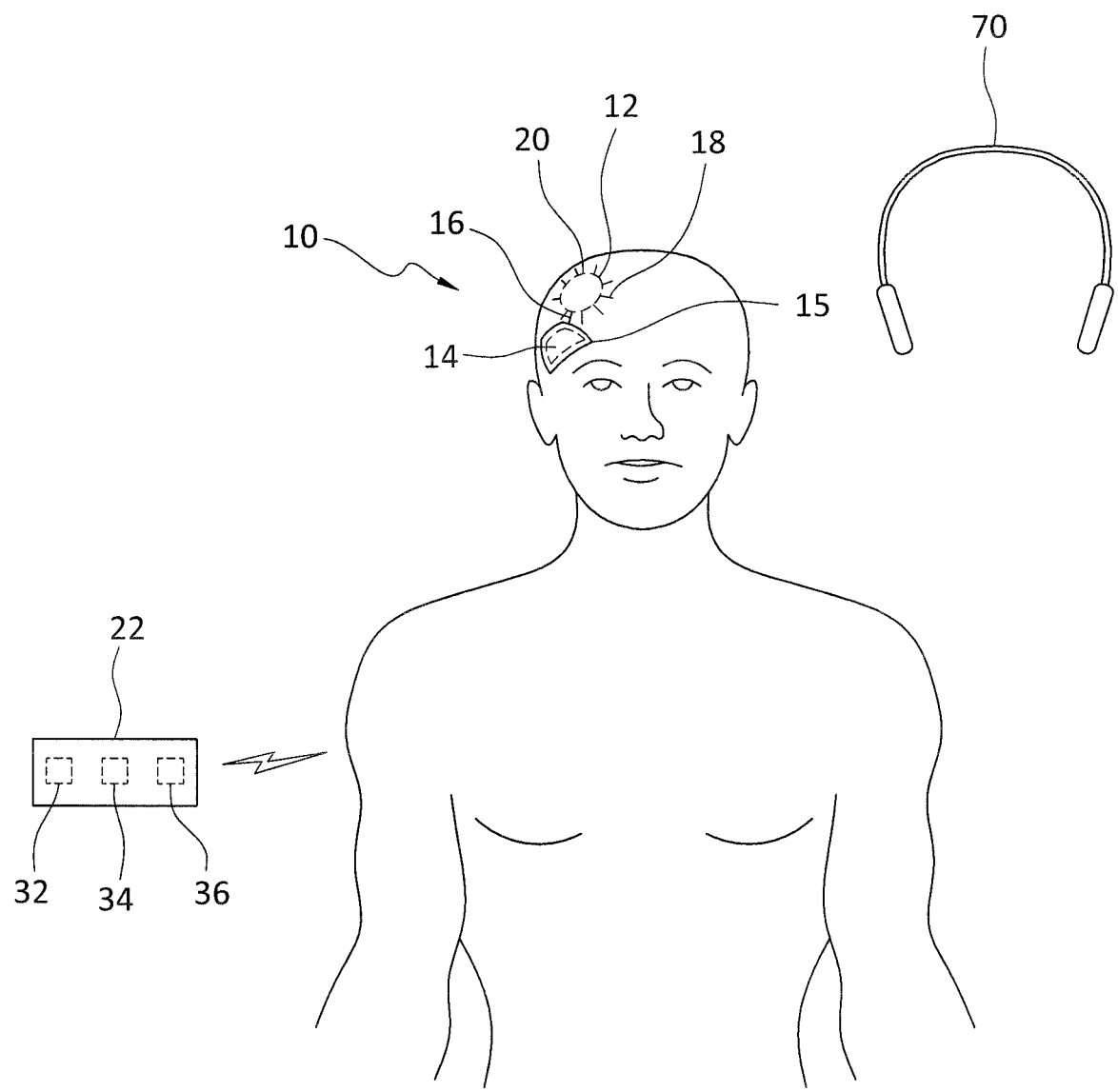
FIG. 1 is a schematic showing a cranial implant and an associated data management and energy system with the cranial implant implanted within a patient.
Figure 2:
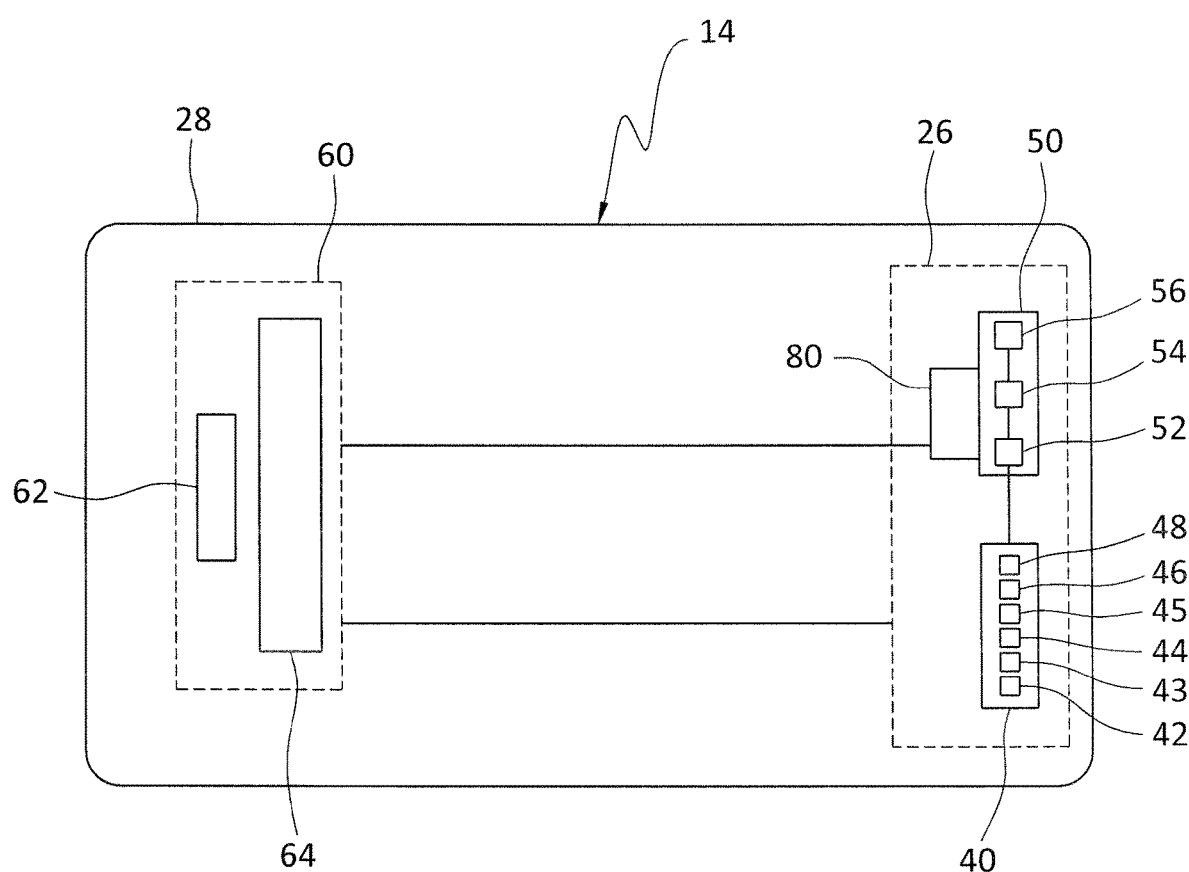
FIG. 2 is a general schematic of the power data management module.
Figure 3:
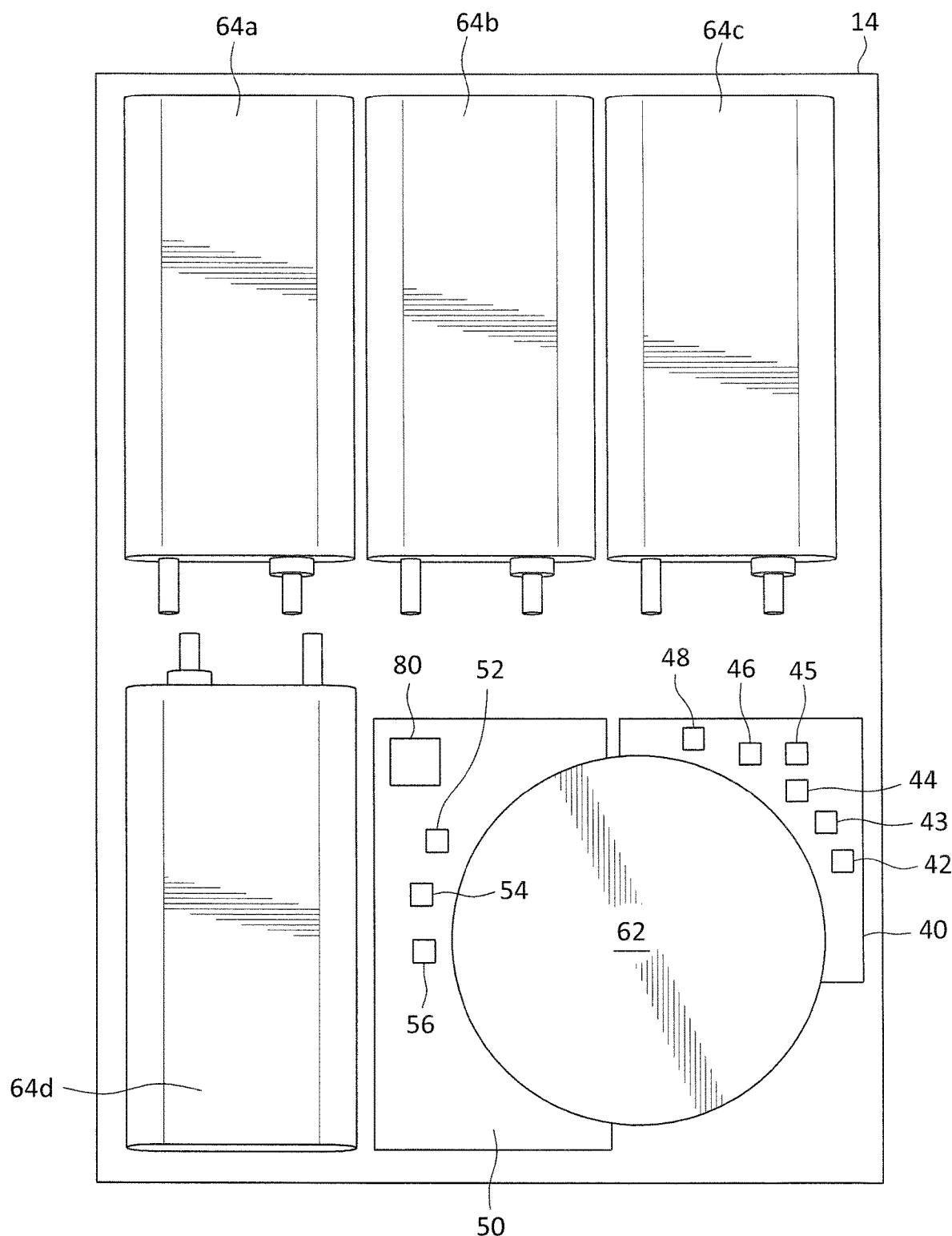
FIG. 3 is a rendering of the power data management module in accordance with an exemplary embodiment (without specific wiring shown).
Figure 4:
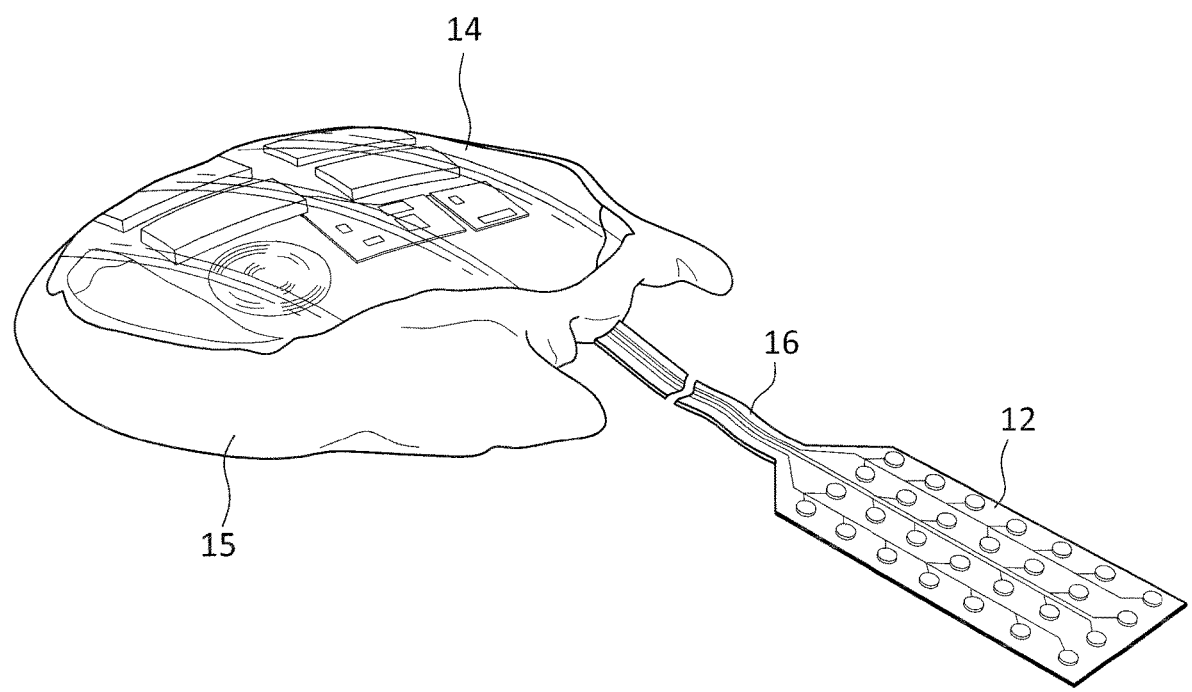
FIG. 4 is a perspective view of the cranial implant, with the power data management module, positioned within the skull.
Figure 5:
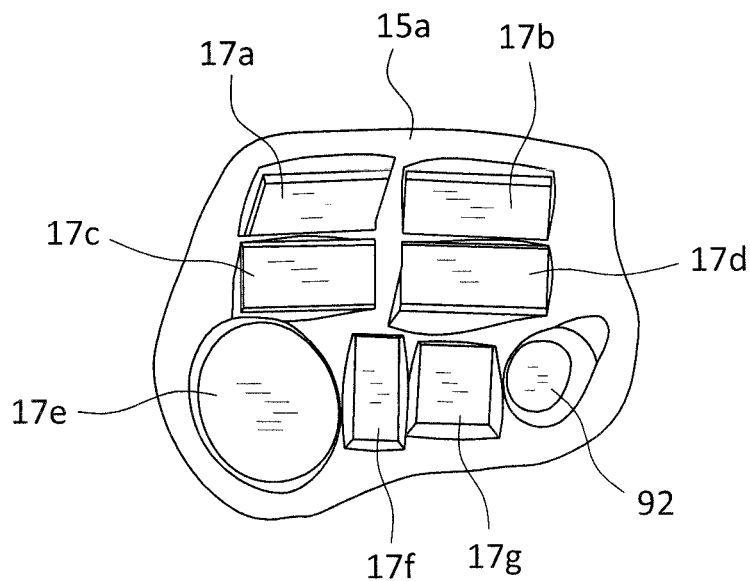
Figure 6:
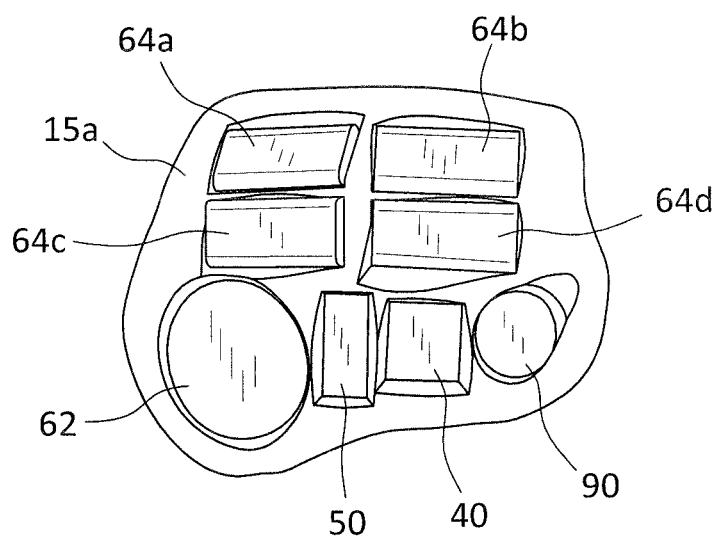
Figure 7:
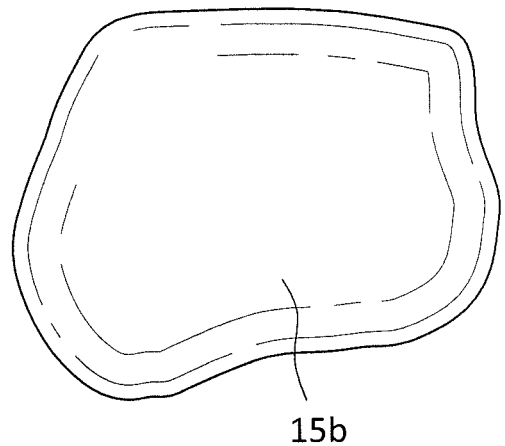
Figures 8A, 8B:
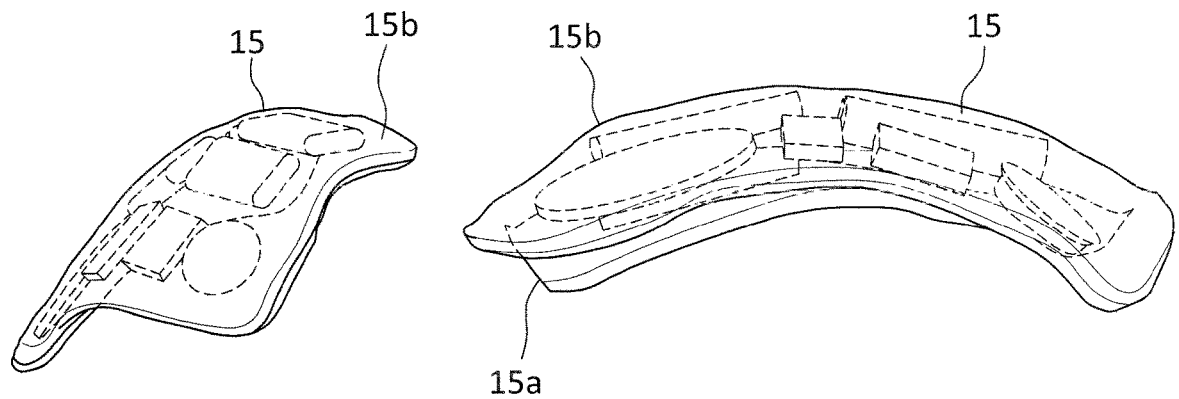
FIGS. 8A and 8B are side views of the cranial implant.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the various figures, an implantable mapping, receiving, and transmitting central nervous system data management and energy system 10 is disclosed. The implantable mapping, receiving, and transmitting central nervous system data management and energy system 10 includes a functional neurological implant 12, a powered data management module 14 mounted within a cranial implant 15, and a data storage and processing unit 22. The implantable mapping, receiving, and transmitting central nervous system data management and energy system 10 is disclosed in U.S. patent application Ser. No. 16/297,863, which is incorporated herein by reference.

Briefly, the functional neurological implant 12 is composed of a neurological device implanted adjacent to, or within, the human brain or spinal cord so as to abut neurologic tissue. The data storage and processing unit 22 is a neurological data processing mechanism capable of receiving, storing, and/or processing neurological data sensed by the functional neurological implant 12. In conjunction with the reception, storage, and/or processing of the neurological data, the data storage and processing unit 22 provides status information regarding the functional neurological implant 12, such as battery charge, data transmission rate, and alerts if there are any issues with data integrity. The powered data management module 14 is constructed to gather the raw signals generated by the functional neurological implant 12 and transmit the signals to the data storage and processing unit 22 in a universally useful format. The powered data management module 14 is constructed to allow for use with prior, current, and future functional neurological implants 12 and data storage and processing units 22 so as to universally allow for communication therebetween.

In accordance with the disclosed embodiment, the powered data management module 14 is integrated into a cranial implant 15 as disclosed in PCT Publication No. PCT/US2016/030447, entitled "LOW-PROFILE INTERCRANIAL DEVICE," filed May 2, 2016, U.S. Patent Application Publication No. 2018/0055640, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, or U.S. Patent Application Publication No. 2019/0209328, entitled "UNIVERSAL LOW-PROFILE INTERCRANIAL ASSEMBLY," filed Nov. 28, 2018, all of which are incorporated herein by reference.

The functional neurological implant 12 and the powered data management module 14 are connected using electrical cabling 16. While electrical cabling 16 is preferably used in connecting the functional neurological implant 12 with the powered data management module 14, other wired and wireless connection mechanisms may be used including, but not limited to, infrared, Bluetooth®, radio signals, and/or optical links.

The data storage and processing unit 22 is remote from the powered data management module 14 (and the functional neurological implant 12). The powered data management module 14 is preferably wirelessly linked to the data storage and processing unit 22. The powered data management module 14 is designed for use with a variety of data storage and processing units 22. By way of example, the data storage and processing unit 22 includes a Bluetooth® transceiver 32, a data storage mechanism 34, and a neurological monitoring system 36 (for example, an electrocorticography monitoring system). While wireless techniques are preferably disclosed above for linking the powered data management module 14 with the data storage and processing unit 22, physical connections, for example, wires may be used in connecting the powered data management module 14 with the data storage and processing unit 22. Further still, the powered data management module 14 may be linked with the data storage and processing unit 22 via a mobile device and/or a variety of other external systems.

In accordance with a preferred embodiment, the functional neurological implant 12 includes brain mapping functionality in the form of a neurological device 20. In accordance with such an embodiment, the functional neurological implant 12 includes sensing elements 18 of the neurological device 20 (see FIG. 1). The sensing elements 18 in accordance with the present invention might be transducers capable of converting an analog signal produced by the body (for example, pressure, temperature, etc.) into an analog electrical signal that can then be used in accordance with the present invention. The sensing elements 18 in accordance with the present invention might also be a traditional electrode that identifies and transmits an electrical signal from the brain. The sensing elements 18 in accordance with the present invention might also be a combination of transducers and electrodes. Regardless, analog sensing elements such as these would result in an analog signal being sent from the sensing element 18 to the powered data management module 14.

While examples are provided above for the structure of the functional neurological implant, it is appreciated other neurological devices may be used in accordance with the present invention and various neurological devices may be used in combination. For example, the sensing elements of the neurological device could be a digital sensing element (for example, a digital electrode). As those skilled in the art will appreciate, the utilization of a digital sensing element in conjunction with the present invention provides for enhanced signal processing as the sensed brain signals are identified and: transmitted by the digital sensing element in a digital format and no analog to digital conversion of the signal is required. Examples of digital sensing elements are found in U.S. Pat. No. 9,420,953, entitled "METHOD FOR IMPLANTING FLEXIBLE AND SCALABLE SENSOR ARRAYS INTO PATIENT TISSUES," which is incorporated herein by reference.

The powered data management module 14 is composed of a data management system 26 and a power system 60. The data management system 26 is constructed for universally interfacing between the functional neurological implant 12 and the data storage and processing unit 22. As such, the powered data management module 14, and in particular, the data management system 26, is designed to universally link to both the functional neurological implant 12 and the data storage and processing unit 22, regardless of whether the manufacturers of either device intended them to work together.

The operational components of the powered data management module 14 are housed within the cranial implant 15. In particular, the data management system 26 and the power system 60 of the powered data management module 14 are housed within the cranial implant 15. The data management system 26 includes a multi-channel input/output 40 for connection with the functional neurological implant 12. Although the term multi-channel input/output is used herein to describe a preferred embodiment of a bus used by the present invention, it is appreciated a variety of bus structures could be utilized by the present invention; for example, single-channel interfaces, multi-channel interfaces, two-way communication interfaces, synchronous or asynchronous timing interfaces, and power transmission interfaces may be used within the spirit of the present invention. The multi-channel input/output 40 is structured to allow for the receipt, whether wired or wireless, of unprocessed raw signals coming from the functional neurological implant 12 to the powered data management module 14, and the subsequent digital conversion and amplification necessary for transmission to the data storage and processing unit 22. The multi-channel input/output 40 is also structured to allow for the transmission of power, where required, from the powered data management module 14 to the functional neurological implant 12.

In accordance with a preferred embodiment, the multi-channel input/output 40 is a CEREPLEX™ (manufactured by BlackRock Microsystems) interface designed to connect with a variety of functional implants. As such the multi-channel input/output 40 includes an analog input 42 directly connected (whether wirelessly or wired) to the functional neurological implant 12, an amplifier 43 and a filter 44 acting upon the analog signals from the functional neurological implant 12 as transmitted via the analog input 42, a multiplexer 45 receiving the amplified and filtered analog signals and transmitting them to an A/D converter 46 for conversion of the analog signals to digital signals, and a digital output 48 transmitting the converted signals from the multi-channel input/output 40 to a transmitter 50, which also forms part of the data management system 26. The transmitter 50 includes a digital input 52 receiving the digital signals from the multi-channel input/output 40, a data storage structure 54, and a Bluetooth® transceiver 56 sending signals to the data storage and processing unit 22.

In accordance with the preferred embodiment, the data management system 26 operates with the following specifications: sixty-four (64) channels of data allowing for a maximum number of sensors utilized in conjunction with the functional neurological implant 12; a 900 hertz sampling rate; 16-bit processing; a low-pass filter set with a cutoff frequency of 450 hertz (for example, for eliminating aliasing and/or artifacts from cable motion and environmental noises); a wireless data transmission rate of 1 MB/second (allowing for operation with current Bluetooth® version 5.0); and a storage capacity of 8 GB of data allowing for approximately 2 hours of operation between transmissions to the data storage and processing unit 22.

In addition to the multi-channel input/output 40 and the transmitter 50, the powered data management module 14 also includes a power system 60 as briefly discussed above. The power system 60 is composed of a power receiver 62 (for example, a wireless charging coil) adapted to receive power from an external power source 70 (whether wired or wireless (for example, a wireless charging headset)) and a battery 64 storing energy for use by the multi-channel input/output 40, transmitter 50, and the functional neurological implant 12. In a disclosed embodiment, the power system 60 includes four 200 milliamp-hour batteries 64*a-d* allowing for 8 hours of operation between charges. As monitoring of battery life is critical to proper operation and monitoring, battery information is regularly transmitted to the data storage and processing unit 22 along with the digital signal data.

Operation of the data management system 26 and the power system 60, that is, the powered data management module 14, is controlled by a microprocessor 80, which also forms part of the powered data management module 14. The microprocessor 80 is preferably integrated with the transmitter 50 (and respectively electrically linked to the power system 60 and the multi-channel input/output 40), although it is appreciated the microprocessor may be formed as a separate unit and linked with the other operational components.

While a preferred embodiment is described above for the powered data management module 14, it is appreciated the powered data management module may contain various combinations of technologies without hindering the desire to allow for universal connection between the functional neurological implant 12 and the data storage and processing unit 22. For example, the powered data management module 14 may include systems for constant recording and "on-board" storage, a master clock that controls recording, librarying technology (i.e., creating data sets), power management systems, and wired and/or wireless transmission mechanisms.

In practice, and after receipt of the unprocessed raw signal from the functional neurological implant 12, the unprocessed raw signal is subjected to analog to digital conversion and amplification to produce a digital signal that is transmitted to the transmitter 50. The digital signal is then buffered in the data storage structure 54 and prepared for transmission by the Bluetooth® transceiver 56 to the data storage and processing unit 22. As the raw signal coming from the functional neurological implant 12 has only been digitally converted and amplified, it is considered to be a universal unprocessed signal that may be used in conjunction with various data storage and processing units 22.

While a battery is disclosed as a power source in a disclosed embodiment, it is contemplated the power system could rely upon other energy sources, for example, energy harvesting systems or inductive power systems. While the various embodiments disclosed above show a single functional neurological implant communicating with the powered data management module, it is appreciated that a plurality of functional neurological implants may communicate with a single powered data management module. Such communication may be achieved either wired or wirelessly.

Referring to FIGS. 5 to 22, a two-part molding process is used in the manufacture of the custom cranial implant 15 with an integrated powered data management module 14 as discussed above with reference to FIGS. 1 to 4. The cranial implant 15, which is composed of a cavity implant 15a and a cap implant 15b, is shown in FIGS. 5, 6, 7, and 8. While the two-part molding process described below is used in conjunction with the integrated powered data management module described above, it is appreciated the two-part molding process described herein may be extended for use with other neurological devices and various neurological devices may be used in combination. For example, the two-part molding process may be implemented in conjunction with ICP (intracranial pressure) devices, neurostimulation devices, therapeutic ultrasound, RF devices, etc. In addition, it is appreciated some of these devices as currently marketed are contained in housings. The traditional housings may not be necessary when the functional components are incorporated into a cranial implant as described herein, thereby saving space and permitting imaging, among other advantages.

The custom cranial implant 15 with the integrated powered data management module 14 is an implantable medical device that encapsulates various electrical components for the purposes of mapping, recording, and transmitting neural activity data. The custom cranial implant 15 not only properly fits within the patient's skull but also encapsulates all of the electrical components of the powered data management module 14. Due to the thickness of the components of the powered data management module 14 (that is, the multi-channel input/output 40, transmitter 50, and power system 60 composed of a power receiver 62 and batteries 64a-d), it is appreciated that portions of the custom cranial implant 15 may need to be bulked laterally beyond the contours of the native cranium. Additionally, the perimeter of the custom cranial implant 15 should match the height of the cranium in order to provide a smooth transition from the cranial implant 15 to the existing cranium.

Temporal bulking can simplify the shape of a cranial implant 15 by reducing the curvature and making the cranial implant 15 flatter in the temporal region. However, not all surgeons desire temporal bulking in a cranial implant. If the cranial implant 15 is designed without temporal bulking, the cranial implant 15 can take on a much more complicated shape, particularly as the cranial implant 15 contours to the sphenoid bone and zygomatic arch.

As to the design of the custom cranial implant 15 with the integrated powered data management module 14, a disclosed embodiment uses MATERIALIZE 3-MATIC™, a data optimization software for computer design in additive manufacturing. As will be appreciated based upon the following disclosure, the cranial implant 15 includes a cavity implant 15a and a cap implant 15b. In accordance with a disclosed embodiment, an initial curve is drawn on the outer surface of a three-dimensional rendering of the skull in the approximate region where the cavity implant 15a with the integrated powered data management module 14 is to be positioned (hemi-craniectomy). The purpose of this curve is to develop tools to help orient and position the components of the powered data management module 14. This curve is not used to determine the outline of the cavity implant 15a with the powered data management module 14. Planes are positioned in regular intervals along the curve from anterior to posterior. References are added to each plane to assist with the construction of a surface. The references include the skull and the curve. Within each plane, a line is drawn along the outer surface of the skull. Using the planes as references, a surface is created that follows the contours of the outer surface of the native skull. The surface is then uniformly offset by 5 mm to create a second surface 5 mm below the original surface. This surface serves as a reference when positioning the components of the powered data management module 14.

STL files of each component of the powered data management module 14 are imported into MATERIALIZE 3-MATIC™. The components are strategically positioned to follow the contours of the second surface, and hence the skull. The components are also positioned to not cut across the surface. By doing so, the components are precisely positioned 5 mm below the outer surface for use in a 5.5 mm thick implant. Because a minimally sized cavity implant 15a is desired, the distance between the components is reduced as much as possible.

A new curve is then drawn on the skull which is used to create a surface large enough to encompass the components but also minimize the footprint of the cranial implant 15 to the extent possible. The surface is created using the original planes in conjunction with the new curve. The surface is then uniformly offset as a solid by 5.5 mm. A 3 mm chamfer is implemented on the perimeter of the cranial implant. Fifteen (15) STL files known as 'component cutters' are imported into MATERIALIZE 3-MATIC™. The component cutters are objects that have the same inner surface shape as the components of the powered data management module 14. However, the top surfaces of the component cutters are much taller than the components of the powered data management module 14 and flare out at angles. The component cutters are also slightly enlarged compared to the components of the powered data management module 14.

The component cutters are used to Boolean subtract cavities 17a-g for the components in the 5.5 mm thick implant. The resulting implant is known as the cavity implant 15a, seen in FIGS. 5 and 6.

Figure 9:
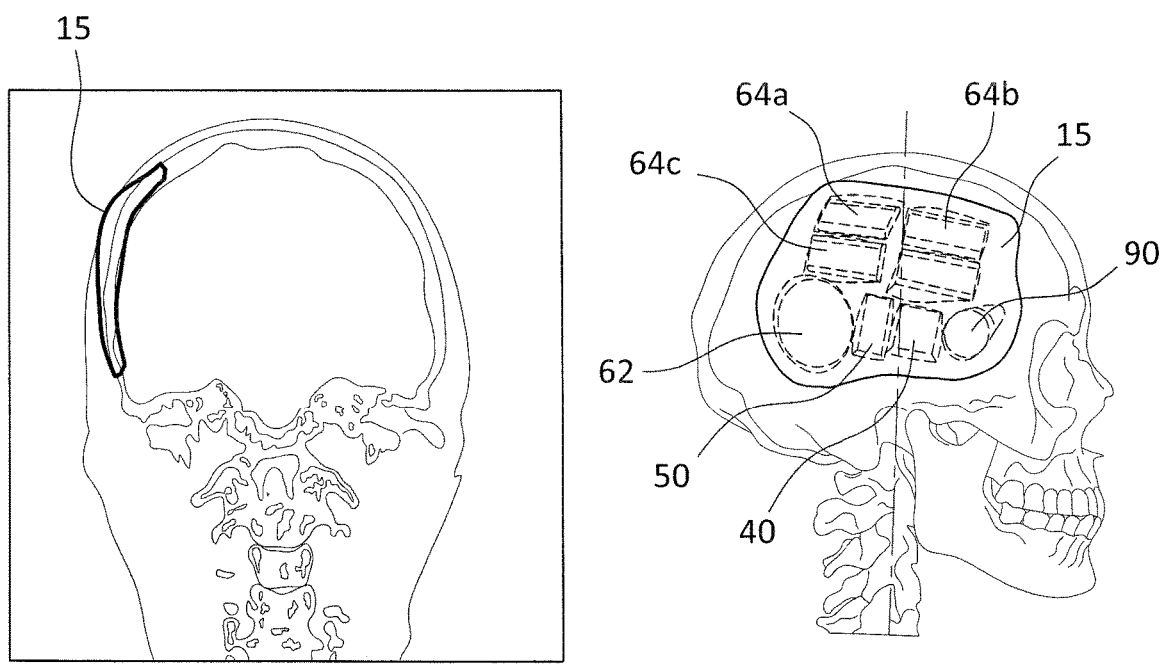

The components of the powered data management module 14 are then wrapped by 1 mm. This serves as a reference to help create a top surface that is to be at least 1 mm above the top surface of the components of the powered data management module 14. The wrapped components of the powered data management module 14 are added as references to the plane. In each plane, sketches are drawn from the curve intersection, along the top surface of the wrapped components of the powered data management module 14, and then back to the other curve intersection. Using the planes as references, a top surface is then generated. The surface is then offset to create a solid. The solid offset and the 5.5 mm thick implant, without the cavities, are merged to create a solid implant, seen in FIG. 7. This implant is known as the cap implant 15b because the top surface, which is created, acts as a cap that is used to encapsulate the components of the powered data management module 14. The cap implant 15b represents the final shape and size of the custom cranial implant 15 with the powered data management module 14, seen in FIGS. 8A and 8B. The position of the final prototype within the skull is shown in FIG. 9.

Figure 10A:
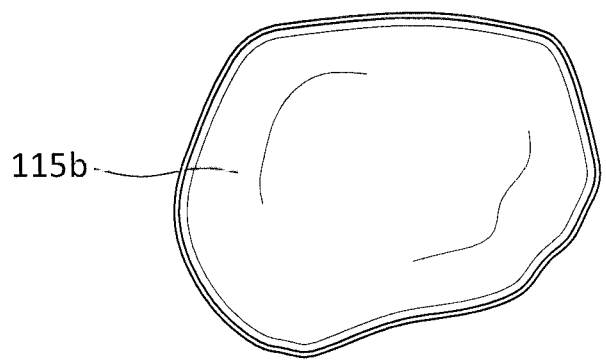
FIGS. 10A and 10B are top and bottom views of the cap master.
Figure 10B:
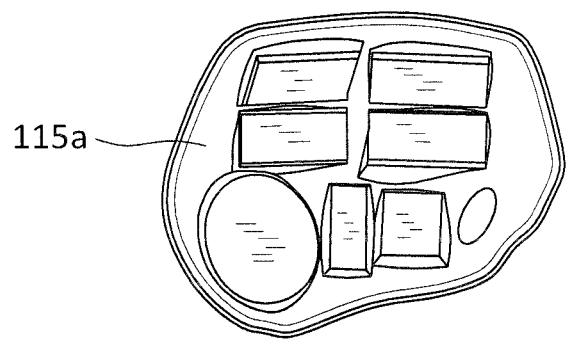
Figure 11A:
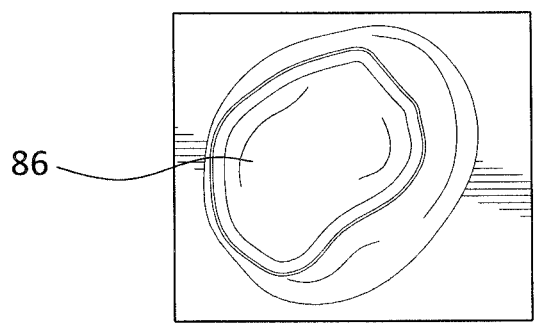
FIGS. 11A and 11B are molds generated based upon the cap master shown in FIGS. 10A and 10B.
Figure 11B:
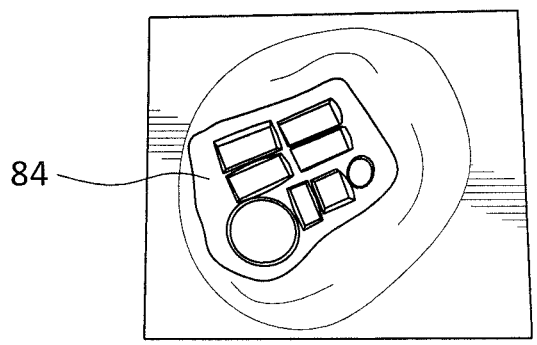
Figure 15:
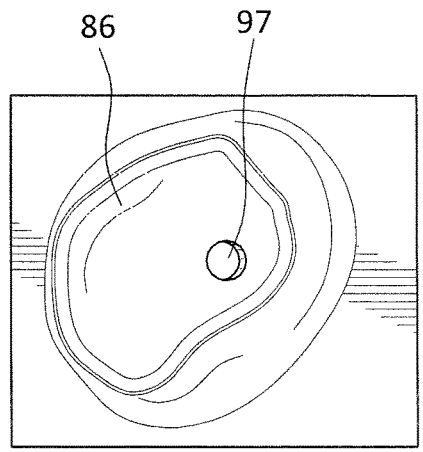

Using a 3D printer, masters of the cavity implant 15a and the cap implant 15b are printed, shown in FIGS. 10A and 10B, and respectively labeled 115a and 115b. A master of the electrode plug 90 is not printed since a previously manufactured electrode plug is used. The master of the cavity implant 115a is used to create a two-part buffstone mold 82 composed of a first mold 84, a second mold 86, and a third mold 88. The first mold 84 is formed around the outer surface of the master of the cavity implant 115a. The second mold 86 is molded around the sides and inner surface of the master of the cavity implant 115a, seen in FIGS. 11A and 11B. Since the cavity implant 15a and the cap implant 15b have the same inner surface and sizes, the second mold 86 is used to cast the third mold 88, which is molded around the outer surface of the master of the cap implant 115b.

In accordance with an embodiment, the first mold 84 and the second mold 86 are prepared in a cleanroom. The following steps pertain to both the first mold 84 and the second mold 86. In practice, the following steps are performed for the first mold 84 and then are repeated again for the second mold 86. The molds are ensured to be clean by wiping the molds using a lint-free paper towel. The mold is further ensured to be dry and free of debris before proceeding. A thin layer of petroleum jelly is wiped over the surface of the mold and any excess petroleum jelly is removed with a lint-free paper towel. Strips of tin foil are cut to an appropriate length, wherein the tin foil should be long enough to cover the length of the mold. It is appreciated two layers of tin foil may need to be overlapped to cover the width of the mold. Thereafter, a strip of tin foil is placed on the mold, the foil is pressed onto the mold (starting from the center and working towards the edges), the foil is smoothed and burnished onto the mold to remove any large wrinkles, bubbles, or any other imperfections, any excess petroleum jelly that is squeezed from under the foil is wiped away, additional layers of tin foil are placed on the mold so that the entire buffstone surface has been covered, and the tin foil mold is wiped to remove any grease or petroleum jelly residue (using a lint-free paper towel).

In accordance with another embodiment, rather than using tin foil to line the mold, MASEL SUPER-SEP™ separating medium may be used to prepare the first mold for casting. Since the first mold represents the top surface of the master of the cavity implant, trying to foil such a complex surface with hard angles can be difficult and can lead to rough implant surfaces. Therefore, a separating medium is used to test its efficacy for creating a smooth barrier between the buffstone and the uncured PMMA (poly (methyl methacrylate)). Two coats of the separating medium are applied to the first mold with 20 minutes between each coat application. The coats are allowed to dry overnight. The mold is packed with uncured PMMA and placed within a heated water bath and allowed to cure at 90° C. for 300 minutes. This is the first curing cycle. It is appreciated that while PMMA is used in accordance with a disclosed embodiment, other synthetic resins may be used where they exhibit similar beneficial material properties.

Once the first and second molds 84, 86 are prepared, a biocompatible casting material, for example, PMMA in accordance with a disclosed embodiment, is mixed for casting the cavity implant 15a. As with the mold processing step presented above, all steps are performed in a cleanroom. The amount of polymer and monomer needed for casting is determined, wherein the weight of the polymer and monomer needed is dependent on the weight of the 3D printed master of the cavity implant 115a. Thereafter, the appropriate amount of polymer is weighed into a clean bowl, the appropriate amount of monomer is weighed into a clean beaker, the contents of the beaker are poured into the bowl with the polymer, and a lid is placed over the bowl and the bowl is kept under the hood. Every 5 minutes, the consistency of the PMMA mixture is checked until the desired consistency is achieved, wherein it is appreciated the mix time should not exceed 30 minutes and the contents of the bowl can be stirred periodically to ensure even mixing.

The cavity implant 15a is then cast. As with the mold processing step presented above, all steps are performed in a cleanroom. Further, and before handling the PMMA, clean gloves must be worn. The PMMA is removed from the bowl. The PMMA is then kneaded, pulled, and folded for 15-30 seconds under a fume hood. The PMMA is removed from under the fume hood and placed within the implant impression within the first mold 84. The PMMA is spread to mostly fill the impression. It is appreciated the PMMA should not be placed outside the perimeter of the impression. The second mold 86 is then placed directly over the first mold 84 and secured to the first mold 84 using bolts. The second mold 86 and the first mold 84 should be parallel to each other as the bolts are tightened to ensure the molds are closing properly. The first mold 84 and the second mold 86 are placed in the hydraulic bench press and pressure is slowly increased until the gauge stabilizes at 5 metric tons. As the pressure is gradually applied, the bolts are continually tightened so they are snug. Once 5 metric tons of pressure is applied, a torque wrench is used to tighten the bolts in a cross pattern to 20 lb-ft. Thereafter, the molds are removed from the press.

The cavity implant 15a is then cured in a cleanroom. A water bath is filled with hot water, at 40±5° C. The first mold 84 and the second mold 86 are placed in the water bath and a thermocouple data logger is placed into the water bath to record temperature data. A programmed water bath cycle is run. When the cycle is complete, the water bath is drained, and the flask is removed from the water bath. The thermocouple data logger is removed, and the temperature graphs are printed and saved. Finally, it is confirmed that the water bath performed the correct curing cycle.

Following the first curing cycle, the PMMA cavity implant 15a is removed and only the outer surface is lightly sanded, as seen in FIG. 12. The sides and inner surface of the cavity implant 15a are not sanded. The electrode plug hole 92 for the electrode plug 90 is sanded to the proper shape by applying sandpaper to a 3D printed plug master 89 and rotating the plug master 89 within the electrode plug hole 92 of the cavity implant 15a. This allows the electrode plug hole 92 within the cavity implant 15a to properly seal with the electrode plug 90 when fully assembled. The cavities 17a-g of the cavity implant 15a only require light sanding for the components of the powered data management module 14 to fit properly.

In a molding/production room, the cavity implant 15a is removed from the first mold 84 and the second mold 86. Before removing the cavity implant 15a from the first and second molds 84, 86, the first and second molds 84, 86 should be cool enough to handle without causing burns. The bolts securing the second mold 86 to the first mold 84 are removed and the second mold 86 is lifted from the first mold 84. The PMMA cavity implant 15a is then removed from the first mold 84. If the cavity implant 15a is stuck to the first mold 84, the first mold 84 may be run under water to help release the cavity implant 15a from the first mold 84. In the event the foil is still stuck to the cavity implant 15a, as much foil as possible is removed from the cavity implant 15a by hand.

The cavity implant 15a is then sanded. In one embodiment, and if necessary, the flashing is removed from the cavity implant 15a by breaking as much of the flashing off by hand and sanding the remaining flashing away using a rotary sander. The top surface of the cavity implant 15a is sanded using a coarse sandpaper, such as 320 grit, to remove any large scratches, bumps, or other imperfections, and the thickness of the top surface of the cavity implant 15a is measured. The cavities 17a-g of the cavity implant 15a are then sanded using coarse sandpaper, such as 320 grit, to remove any imperfections which would prevent the components of the powered data management module 14 from properly residing within the cavities 17a-g. The shape and positioning of the cavities 17a-g are checked by placing replica components of the powered data management module 11 within the cavities 17a-g and the shape of the cavities 17a-g is modified to ensure the components of the powered data management module 14 properly reside within the cavities 17a-g. The electrode plug hole 92 is then sanded and shaped by placing sandpaper around the electrode plug 90, placing the electrode plug 90 in the electrode plug hole 92 within the cavity implant 15a, rotating the electrode plug 90 to allow the sandpaper to shape the electrode plug hole 92 in the cavity implant 15a, and periodically checking the sandpaper and replacing if it is becoming worn. Throughout the sanding process, the fit of a PMMA electrode plug 90 with the electrode plug hole 92 in the cavity implant 15a is periodically checked.

In one embodiment, the fit is checked by placing the electrode plug 90 in the cavity implant 15a, applying pressure to the electrode plug 90 using a hand and flipping the cavity implant 15a so the inner surface is facing upwards. With the cavity implant 15a in the concave position, water is placed over the electrode plug 90 and observed for water leaks between the implant/plug interface. If a leak is observed, sanding the cavity implant 15a is continued, if necessary, and if no leaks are observed, sanding the cavity implant 15a is stopped. Care should be taken to not oversand the electrode plug hole 92 in the cavity implant 15a.

The inner surface of the cavity implant 15a is then sanded and polished. Using progressively finer sandpaper, the inner surface of the cavity implant 15a is sanded until it is smooth. Wet sanding should be used for higher grit sandpapers. Once all major scratches are removed, the inner surface of the cavity implant 15a is polished using a polishing compound and a polishing wheel. One should then check to see if all scratches and imperfections have been removed before proceeding and make certain that the perimeter of the cavity implant 15a is not altered along the edge thereof. One should also check the cavity implant 15a to confirm it does not contain any major defects or debris within the cavity implant 15a.

The cavity implant 15a is then cleaned with dish soap. After sanding is complete, dish soap and a nylon brush are used to scrub the cavity implant 15a to remove all debris and the cavity implant 15a is rinsed with warm water and dried with a lint-free cloth.

The cavity implant 15a is then moved to the cleanroom and cleaned with LIQUINOX®, a cleaning liquid detergent. In particular, using a 1% LIQUINOX® solution, the implant is scrubbed with a nylon brush until it is free of debris, thoroughly rinsed using deionized water, and the implant is placed on a drying rack to air dry.

Figure 16:
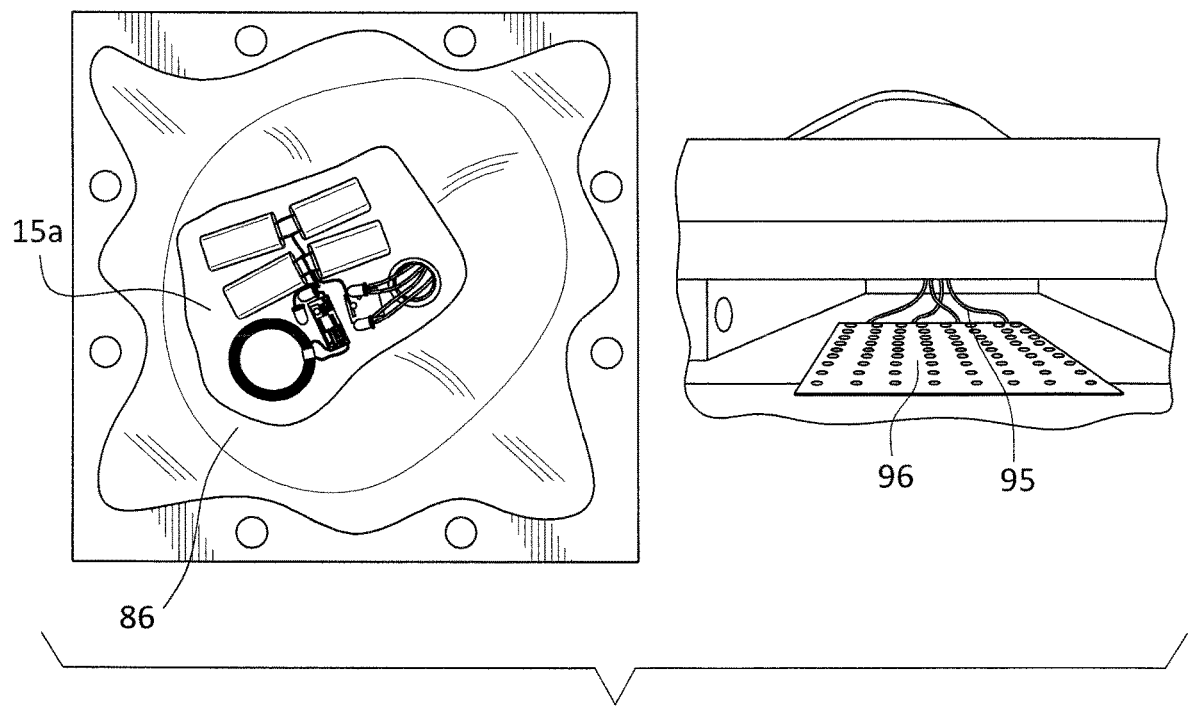

Referring to FIGS. 15 to 19, the secondary curing cycle is now disclosed. As is discussed below in detail, to make room for the electrode leads 95 during the secondary curing cycle, a hole 97 is drilled through the second mold 86 where the electrode leads 95 are to exit the cavity implant 15a, seen in FIG. 15. The second mold 86 and the third mold 88 are then foiled. The PMMA cavity implant 15a is placed on the second mold 86. The components of the powered data management module 14 are placed within the respective cavities 17a-g and the electrode grid 96 is passed through the bottom of the cavity implant 15a, down the hole 97 in the second mold 86, and out to the exterior of the second mold 86, as seen in FIG. 16. Uncured PMMA is carefully placed on the surface of the cavity implant 15a and components of the powered data management module 14, with caution taken to avoid shifting the PMMA layer. The third mold 88 is then lowered onto the second mold 86. The second and third molds 86, 88 are closed and placed into the water bath to cure. The electrode grid 96 is secured to the outside of the second and third molds 86, 88 to prevent it from becoming tangled in the washer bath's immersion circulator. The electrode grids are submerged during the entirety of the curing cycle.

In particular, the second mold 86 is modified in the molding/production room to accommodate the electrode grid housing 98 in the following manner. The master of the cavity implant 115a is placed on the second mold 86 and the location of the electrode plug hole 92 is marked on the second mold 86. Using a long and relatively small diameter drill bit, a pilot hole is drilled through the second mold 86. The pilot hole is angled so that it originates within the marking created for the electrode plug 90 and exits through the opening in the bottom plate. Once a pilot hole has been drilled at the correct trajectory, a larger drill bit, that is, a drill bit having a diameter larger than the thickness of the electrode grid housing 98, is used to drill the larger hole 97 in the second mold 86 at the same trajectory as the pilot hole. It is appreciated that several holes may need to be drilled to accommodate the size of the electrode grid housing 98. Thereafter, and using a standard drill bit, the hole 97 is shaped so it is smooth, with an oval shape that is large enough to accommodate the electrode grid housing 98. After the hole 97 has been drilled, both the second mold 86 and the third mold 88 are thoroughly cleaned using dish soap and a nylon brush to remove any debris.

The second mold 86 and the third mold 88 are then prepared in the cleanroom for casting the final implant. The following steps pertain to both the second mold 86 and the third mold 88, and one performs the following steps for the second mold 86 and then repeats them for the third mold 88. The mold is ensured to be clean by wiping the mold using a lint-free paper towel. The mold is then ensured to be dry and free of debris before proceeding. A thin layer of petroleum jelly is wiped over the surface of the mold and any excess petroleum jelly is removed with a lint-free paper towel. Strips of tin foil are cut to an appropriate length, wherein the tin foil is long enough to cover the length of the mold and two layers of tin foil may need to be overlapped to cover the width of the mold. Thereafter, a strip of tin foil is placed on the mold, the foil is pressed onto the mold (starting from the center and working towards the edges), the foil is smoothed and burnished onto the mold to remove any large wrinkles, bubbles, or any other imperfections, any excess petroleum jelly that is squeezed from under the foil is wiped away, additional layers of tin foil are placed on the mold so that the entire surface of the mold has been covered, and the tin foil mold is wiped to remove any grease or petroleum jelly residue (using a lint-free paper towel). For the second mold 86, an 'X' shape is cut into the foil above the hole in the mold and the foil is pressed down into the walls of the hole, and the cleaned cavity implant 15*a* is placed on the second mold 86.

The components of the powered data management module 14 are then prepared for casting in the cleanroom. The components of powered data management module 14 are carefully and fully removed from their packaging and checked to ensure that all the components of the powered data management module 14 are safe from electrostatic discharges. The electrode grid housing 98 and the bolts used to hold it together are obtained. The electrode grid housing 98 is properly cleaned before proceeding.

After checking and cleaning, the electrode grid 96 is placed within the electrode grid housing 98. The electrode grid housing 98 is designed to hold a 64-channel subdural electrode grid 96 when it is folded onto itself. Two columns of the electrode grid 96 are placed into the electrode grid housing 98, with the exposed electrode leads 95 facing upwards, while avoiding bending and flexing the electrode grid 96 as much as possible when inserting it into the electrode grid housing 98. The electrode grid 96 is folded along the region where no wires reside and another two columns of the electrode grid 96 are placed into the electrode grid housing 98. If done correctly, the exposed electrode pads should be facing each other within the electrode grid housing 98. The electrode grid 96 is folded twice more to fit the remaining portion of the electrode grid 96 within the electrode grid housing 98. As each portion of the electrode grid 96 is folded into the electrode grid housing 98, the leads from that portion of the electrode grid 96 are pressed into the neck of the electrode grid housing 98 to ensure it is properly seated. Once the electrode grid 96 is within the electrode grid housing 98, the electrode grid 96 of the electrode grid housing 98 is placed over the electrode grid 96, the lid is pressed down, and it is ensured that it is properly seated on the electrode grid housing 98 and the electrode grid 96 is not being pinched. Small bolts are placed through the holes in the lid and electrode grid housing 98 and gradually tightened in a cross pattern. The components of the powered data management module 14 are placed within the cavity implant 15*a*.

The electrode grid housing 98 is fed through the cavity implant 15*a* and through the hole in the second mold 86. Once the electrode grid housing 98 is through the second mold 86, the components of the powered data management module 14 are lowered into their respective cavities within the cavity implant 15*a*. It is then ensured that the electrode plug 90 is properly seated within the cavity implant 15*a*.

The PMMA for casting the cap implant 15*b* is then mixed. All steps are performed in a cleanroom. The amount of polymer and monomer needed for casting is determined, wherein the weight of the polymer and monomer needed is dependent on the weight of the 3D printed cavity master. Thereafter, the appropriate amount of polymer is weighed (under the fume hood) into a clean bowl, the appropriate amount of monomer is weighed into a clean beaker, the contents of the beaker are poured into the bowl with the polymer, and a lid is placed over the bowl and the bowl is kept under the hood. Every 5 minutes, the consistency of the PMMA mixture is checked until the desired consistency is achieved, wherein it is appreciated the mix time should not exceed 30 minutes and the contents of the bowl can be stirred periodically to ensure even mixing.

The cap implant 15*b* is then cast. As with the mold processing step presented above, all steps are performed in a cleanroom. The PMMA is removed from the bowl. The PMMA is then kneaded, pulled, and folded for 15-30 seconds under the fume hood. The PMMA is removed from under the hood and placed within the cavity implant 15*a* and the PMMA is spread to mostly cover the cavity implant 15*a* surface. The PMMA should not be shifted after it has been placed over the components of the powered data management module 14. The third mold 88 is then directly secured to the second mold 86 using the appropriate length bolts. The second mold 86 and the third mold 88 are parallel to each other as the bolts are tightened to ensure the molds can close properly. The second mold 86 and the third mold 88 are placed in the hydraulic bench press. When placing the molds in the press, the electrode grid housing 98 and leads are fed through the bottom plate on the press. Using the handle to crank the press, pressure is slowly increased until the gauge stabilizes at 5 metric tons. As the pressure is gradually applied, the bolts are continually tightened so they are snug. Once 5 metric tons of pressure is applied, a torque wrench is used to tighten the bolts in a cross pattern to 20 lb-ft. Thereafter, the second and third molds 86, 88 are removed from the press.

The cap implant 15*b* is then cured in a cleanroom. A water bath is filled with hot water, at 40±5° C. The second and third molds 86, 88 are placed in the water bath. The second and third molds 86, 88 are oriented such that the leads are exiting from the top of the second and third molds 86, 88 and the electrode grid housing 98 is placed on the top of the second and third molds 86, 88. A thermocouple data logger is placed into the water bath to record temperature data. A programmed water bath cycle is run. When the cycle is complete, the water bath is drained, and the flask is removed from the water bath. The data logger is removed, and the temperature graphs are printed and saved. Finally, it is confirmed that the water bath performed the correct curing cycle.

The cap implant 15*b* is then removed from the second mold 86 and the third mold 88. Before removing the cap implant 15*b* from the second and third molds 86, 88, the second and third molds 86, 88 should be cool enough to handle without causing burns. The bolts securing the second mold 86 to the third mold 88 are removed and the second mold 86 is lifted from the third mold 88. The second mold 86 is lifted up and around the electrode grid housing 98. The PMMA cap implant 15b is then removed from the second mold 86.

The electrode plugs 90 used in accordance with the present invention optimize the passage of electrode leads 95 from the powered data management module 14 through the cranial implant 15 and to the electrode grid 96. The electrode plug 90 includes a plug housing 99 having an upper surface 99a, a lower surface 99b, and side walls 99c extending between the upper surface 99a and the lower surface 99b along the perimeter of the plug housing 99. The plug housing 99 is constructed with a circular profile, although the plug housing 99 could be constructed with other profiles if dictated by specific applications or needs.

The side wall 99c of the plug housing 99 exhibits a taper as it extends from the upper surface 99a to the lower surface 99b. As such, the upper surface 99a has a larger diameter than the lower surface 99b. The electrode plug hole 92 includes a similar shape, that is, the electrode plug hole 92 includes a larger diameter along the upper surface than the lower surface. By providing the plug housing 99 and the electrode plug hole 92 with tapered mating surfaces, a predictable fit is achieved where the electrode plug 90 ultimately seats at a desired position within the electrode plug hole 92.

As mentioned above, the electrode plug 90 provides for the passage of the electrode leads 95 from the powered data management module 14 through the cranial implant 15 and to the electrode grid 96. This is achieved by forming a plurality of holes 100 in the electrode plug 90, wherein the holes 100 are shaped and dimensioned (for example, 1.5 mm diameter holes) to allow for the passage of the electrode leads 95 from the upper surface to the lower surface. Optimal passage of the electrode leads 95 through the electrode plug 90 is achieved by obliquely orienting the holes 100 relative to the planar surface defined by the upper and lower surfaces 99a, 99b of the electrode plug 90 (for example, at a 40 degree angle), as seen in FIGS. 13A, 13B, and 13C. By obliquely orienting the holes 100, sharp angles are minimized as the electrode leads 95 pass through the electrode plug 90.

In accordance with a disclosed embodiment, four electrode leads 95 for the subdural electrode grid 96 are passed through the holes 100 in the electrode plug 90. The tail collars from the electrode leads 95 are then cut and the bare inner wires are exposed. The wires from the electrode leads 95, as well as the wires for the powered data management module 14, are soldered in a predetermined manner, as seen in FIG. 14. The length of the wire exiting the implant is to be approximately 15 mm long.

Figure 17:
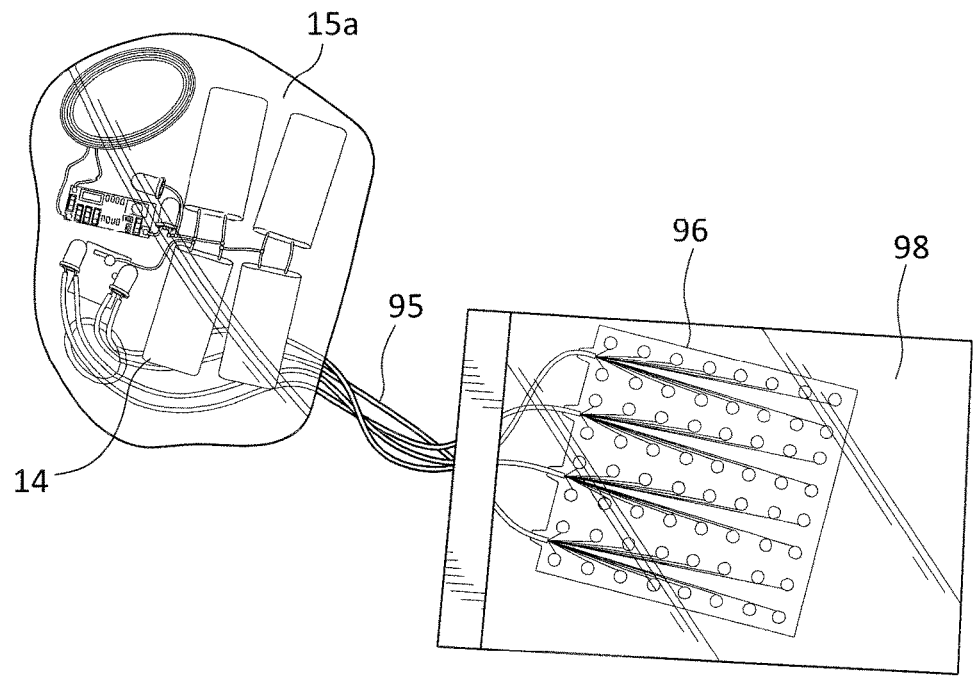
Figure 18:
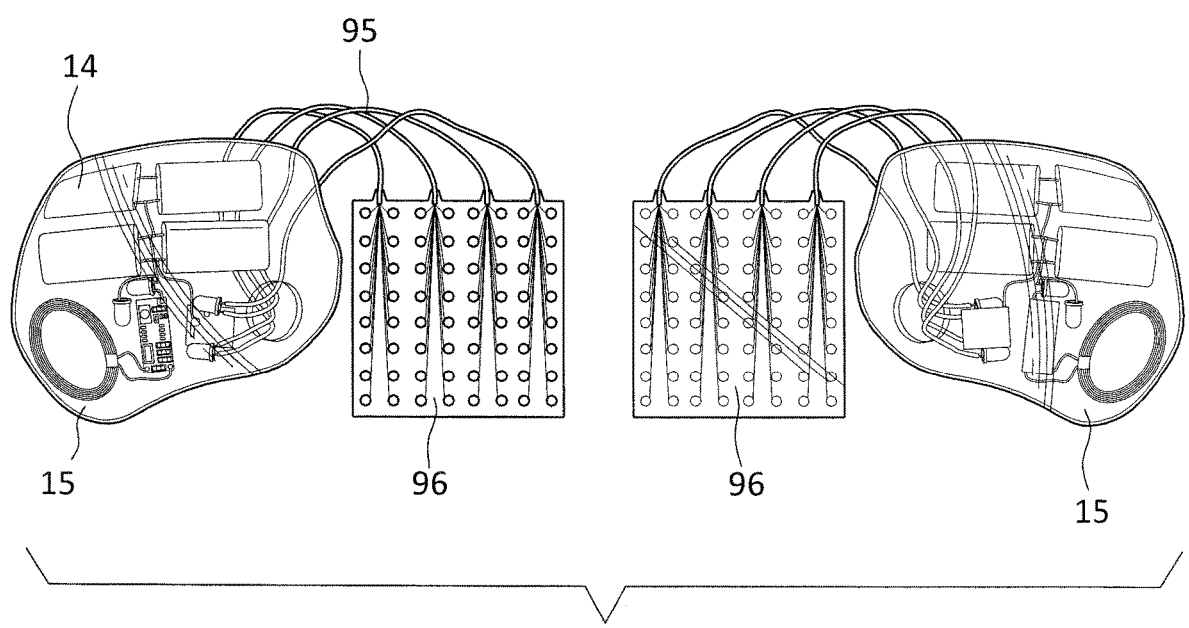
Figure 19:
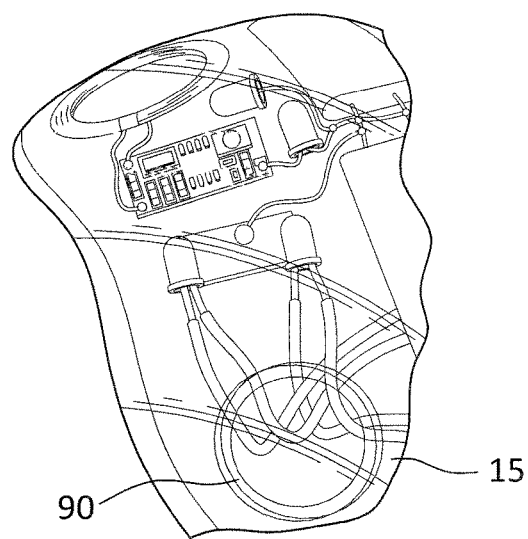
Figure 20:
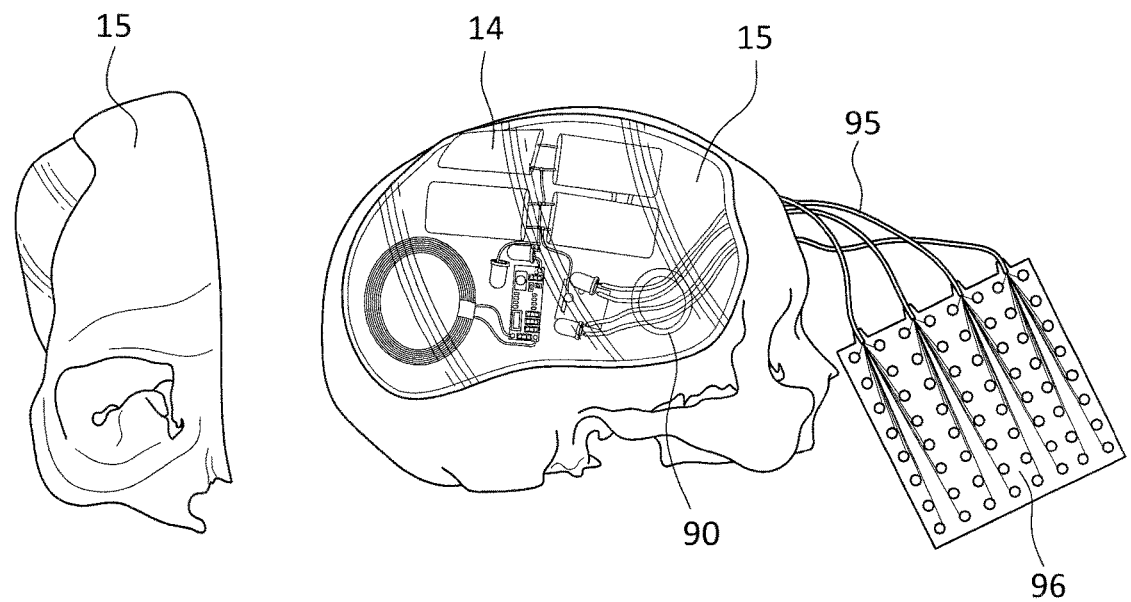

Following the secondary curing cycle, the cranial implant 15 is removed and the functionality of the LEDs is tested to confirm they survived the curing cycle. The electrode grid 96 is placed with a plastic bag and sealed with tape to prevent it from becoming damaged during sanding and polishing, as seen in FIG. 17. The entire implant, both outer and inner surface, is then sanded and polished, as seen in FIG. 18. The functionality of the LEDs is tested again to ensure the electronics did not sustain damage during the manufacturing process, as seen in FIG. 19. The cranial implant 15 is placed within its respective host bone to ensure the implant fits properly following the manufacturing process, as seen in FIG. 20. Thickness measurements are recorded throughout the production process, as seen in FIGS. 21 and 22. For example, Figurer 21 shows measurement were taken comparing the thickness of the printed cavity master and the PMMA cavity implant after light sanding (top). Text identifies the thickness of the printed master and the thickness of the PMMA cavity implant. The measurements were taken comparing the thickness of the printed cap master and the PMMA cap implant. FIG. 22 shows measurements of the final footprint. The length of the leads exiting from the implant is approximately 15 mm long.

Designing the cavity implant 15a to be as thick as possible is advantageous for numerous reasons. The thicker implant allows the cavities to be deeper within the cavity implant 15a, which provides more support to the components of the powered data management module 14 which resides in the cavities. By providing more support, the deeper cavities reduce the possibility of component migration during the secondary curing cycle. Additionally, because the components of the powered data management module 14 can sit deeper within the cavity implant 15a, less of the component is exposed above the top surface of the cavity implant 15a. This means the cap implant 15b of the cranial implant 15 can maintain a lower profile while still successfully encapsulating the components of the powered data management module 14. Reducing the overall profile of the cranial implant 15 is not only beneficial for the patient's aesthetic appearance, but it also reduces the tension on the scalp when the surgical incision is closed during implantation. Furthermore, because the cap implant 15b of the cranial implant 15 can maintain a lower profile due to the deeper cavities, the transition between the cap implant 15b and the surface of the cavity implant 15a can be smoother since the components of the powered data management module 14 are not as prominent above the surface of the cavity implant 15a. This will improve the smooth and fluid appearance of the surface of the implant.

For this 5.5 mm thick cavity implant 15a, the cavities were designed to be 5 mm deep. While the depth of material between the bottom surface of the components of the powered data management module 14 and the inner surface of the cranial implant 15 is designed to be only 0.5 mm, that thickness will increase in the PMMA cranial implant 15 due to expansion. Therefore, the thickness of the cavities is intentionally designed to be thinner to account for expansion observed within the PMMA cranial implant 15. The desired PMMA cavity thickness is 1 mm.

After the cavity implant 15a is demolded, only the top surface of the cavity implant 15a is sanded using 320 grit sandpaper. The sides and inner surface are not sanded in order to preserve its shape so it can properly fit with the second mold 86 during the secondary curing cycle. By having the cavity implant 15a fit with the second mold 86, PMMA is less likely to migrate down the side and underneath the cranial implant 15 during the secondary curing cycle. Conversely, by not sanding and polishing the inner surface before the secondary curing cycle, it must be done following the secondary curing cycle after the electrode leads have been implanted. Sanding and polishing the inner surface could cause potential damage to the leads if care is not taken to protect them.

The integrity of the electrical connection was maintained throughout the secondary curing cycle. All LEDs were successfully illuminated which means the curing process did not pose a risk to the integrity of the electrical connections.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A two-part molding process, the molding process comprising:
   creating a computer-based design of a cranial implant including a cavity implant and a cap implant;
   creating a first mold, a second mold, and a third mold;
   casting the cavity implant from resin;
   curing the cavity implant;
   removing the cavity implant from the first mold and the second mold;
   drilling a hole through the second mold where electrode leads are to exit the cavity implant;
   placing the cavity implant on the second mold and placing components of a functional neurological implant within respective cavities;
   placing uncured resin on the cavity implant and components of the functional neurological implant, lowering the third mold onto the second mold, closing the second and third molds and curing the resin;
   preparing the components of the functional neurological implant for casting;
   casting the cap implant, wherein the third mold is directly secured to the second mold and the second mold and the third mold are placed in a press;
   curing the cap implant; and
   removing the cranial implant and testing.

2. The molding process according to claim 1, wherein the resin is poly (methyl methacrylate).

3. The molding process according to claim 1, wherein creating the first mold, the second mold, and the third mold includes forming the first mold around an outer surface of a master of the cavity implant, molding the second mold around sides and inner surface of the master of the cavity implant, and casting the third mold based upon the second mold.

4. The molding process according to claim 1, wherein casting the cavity implant from resin includes spreading the resin to mostly fill an impression of the first mold, placing and securing the second mold directly over the first mold, applying pressure to the first mold and the second mold, and removing the first mold and the second mold.

5. The molding process according to claim 1, further including creating a master of the cavity implant and a master of the cap implant.

6. The molding process according to claim 1, further including, after curing the cavity implant, sanding the cavity implant.

7. The molding process according to claim 1, further including, after placing the cavity implant on the second mold and placing components of the functional neurological implant within respective cavities, passing an electrode grid is through a bottom of the cavity implant, down the hole in the second mold, and out to an exterior of the second mold.

8. The molding process according to claim 7, wherein the electrode grid is secured to an outside of the second and third molds to prevent it from becoming tangled.

9. The molding process according to claim 8, further including, after preparing the components of the functional neurological implant for casting, feeding an electrode grid housing through the cavity implant and through the hole in the second mold and subsequently lowering the components of the powered data management module into cavities within the cavity implant.

10. The molding process according to claim 1, further including modifying the second mold to accommodate an electrode grid housing.

11. The molding process according to claim 10, wherein modifying includes placing a master of the cavity implant on the second mold, marking a location of an electrode plug hole on the second mold, and drilling a hole through the second mold.

12. The molding process according to claim 1, wherein the molding process is for manufacturing an implantable data management and energy system that includes a functional neurological implant, a powered data management module mounted within the cranial implant, and a data storage and processing unit.

13. The molding process according to claim 12, wherein the powered data management module includes a multi-channel input/output, a transmitter, and a power system comprised of a power receiver and batteries.

14. The molding process according to claim 12, wherein the functional neurological implant is a neurological device implanted to abut neurologic tissue.

15. The molding process according to claim 12, wherein the data storage and processing unit is a neurological data processing mechanism capable of receiving, storing, and/or processing neurological data sensed by the functional neurological implant.

16. The molding process according to claim 15, wherein data storage and processing unit provides status information regarding the functional neurological implant, such as battery charge, data transmission rate, and alerts if there are any issues with data integrity.

17. The molding process according to claim 12, wherein the functional neurological implant and the powered data management module are connected using electrical cabling.

18. The molding process according to claim 12, wherein the data storage and processing unit is wirelessly linked to the data storage and processing unit.

19. The molding process according to claim 12, wherein the functional neurological implant includes brain mapping functionality.

20. The molding process according to claim 1, wherein the functional neurological implant is a powered data management module.

* * * * *